(12) United States Patent
Saxena

(10) Patent No.: US 8,835,121 B2
(45) Date of Patent: Sep. 16, 2014

(54) MODIFIED METHOD OF AGGLUTINATION TO DETECT INFECTIONS CAUSED BY MICROORGANISMS

(75) Inventor: Hari Mohan Saxena, Ludhiana (IN)

(73) Assignees: Department of Biotechnology, New Delhi (IN); Guru Angad Dev Veterinary and Animal Sciences University, Ludhiana (IN)

( * ) Notice: Subject to any disclaimer, the term of this patent is extended or adjusted under 35 U.S.C. 154(b) by 189 days.

(21) Appl. No.: 13/499,418

(22) PCT Filed: Sep. 16, 2010

(86) PCT No.: PCT/IN2010/000624
§ 371 (c)(1),
(2), (4) Date: Jun. 14, 2012

(87) PCT Pub. No.: WO2011/039775
PCT Pub. Date: Apr. 7, 2011

(65) Prior Publication Data
US 2012/0244552 A1 Sep. 27, 2012

(30) Foreign Application Priority Data
Sep. 30, 2009 (IN) .......................... 1345/DEL/2009

(51) Int. Cl.
*G01N 33/53* (2006.01)
*G01N 33/569* (2006.01)
*C12Q 1/04* (2006.01)

(52) U.S. Cl.
CPC ...... *G01N 33/56911* (2013.01); *G01N 2333/23* (2013.01); *C12Q 1/04* (2013.01)
USPC ............ 435/7.1; 435/7.5; 435/7.92; 436/501; 436/518

(58) Field of Classification Search
None
See application file for complete search history.

(56) References Cited

U.S. PATENT DOCUMENTS 7,166,476 B2 * 1/2007 Shigenobu et al. ........... 436/536
2012/0034617 A1 * 2/2012 Cheung et al. ............... 435/6.15

OTHER PUBLICATIONS

Blasco et al., Efficacy of different Rose Bengal and complement fixation antigens for the diagnosis of *Brucella melitensis* infection in sheep and goats, The Veterinary Record, Apr. 16, 1994, pp. 415-420, vol. 134.
Chachra et al, "Comparative efficacy of Rose Bengal plate test, standard tube agglutination test and Dot ELISA in immunological detection of antibodies to *Brucella* abortus in sera", Journal of Bacteriology Research, Jun. 2009, pp. 30-33, vol. 1(3).
Joint FAO/WHO Expert Committee on Brucellosis, Sixth Report, World Health Organization Technical Report Series 740, 1986, pp. 1-132, World Health Organization, Geneva.
Lucero et al., Buffered Plate Antigen Test as a Screening Test for Diagnosis of Human Brucellosis, Journal of Clinical Microbiology, May 1998, pp. 1425-1427, vol. 36, No. 5.
Sarumathi et al., "Comparison of Avidin—Biotin ELISA with RBPT and STAT for screening of antibodies to bovine brucellosis", Indian Vet. J., Nov. 2003, pp. 1106-1108, vol. 80.

* cited by examiner

*Primary Examiner* — Gary W Counts
(74) *Attorney, Agent, or Firm* — The Webb Law Firm

(57) ABSTRACT

Provided herein is a modified method of agglutination to detect infections caused by microorganisms including the steps of staining the test serum, plasma or blood or purified antibodies with a protein stain; mixing serum, plasma or blood with stained antibodies with an equal quantity of colored antigen particles on a glass slide; adding diluted Anti-globulin conjugated with Biotin to the mixture; subjecting the mixture to the step of mixing, adding diluted Avidin (preferably tagged with a visible indicator) to the mixture and thoroughly mixing all the ingredients.

7 Claims, 2 Drawing Sheets

Fig. 1. Normal agglutination with antigen and positive serum.
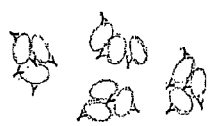
Fig. 2. Enhanced agglutination with antigen, positive serum and (a) IgG or (b) IgM antiglobulins.
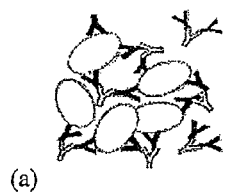 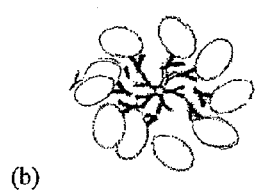
(a)                    (b)
Fig. 3. Superagglutination with antigen, positive serum, biotinylated Antiglobulin and Avidin.
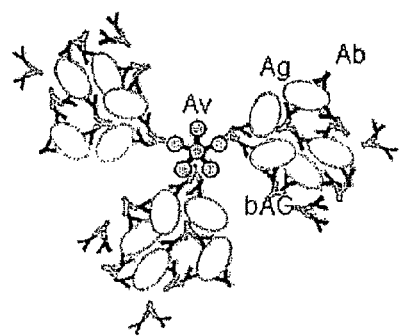

Fig. 4. Normal Agglutination caused by antigen and positive serum.
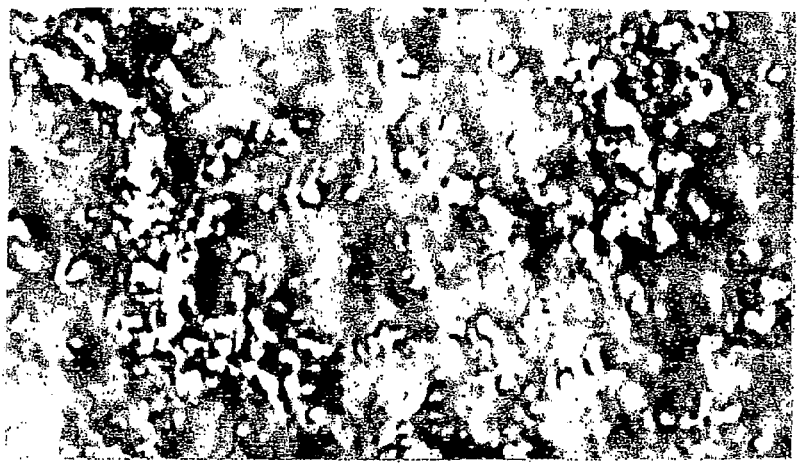
Fig. 5. Superagglutination with biotinylated antiglobulin and Avidin (Gross).
Fig. 6. Superagglutination with biotinylated antiglobulin and Avidin (microscopic).
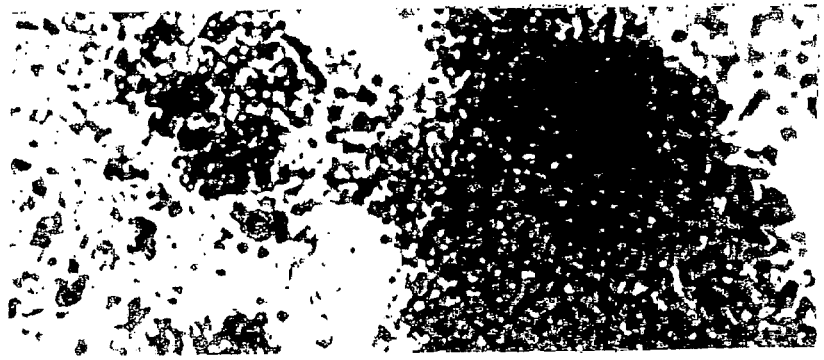

MODIFIED METHOD OF AGGLUTINATION TO DETECT INFECTIONS CAUSED BY MICROORGANISMS

FIELD OF INVENTION

This invention relates to a modified method of agglutination to detect infections caused by microorganisms.

This invention also relates to a highly sensitive agglutination test named as "Superagglutination Test" to diagnose infections caused by various microorganisms and to avoid false positive and false negative results commonly obtained with the conventional agglutination tests.

BACKGROUND OF THE INVENTION

Agglutination tests can be used as qualitative tests to assay for the presence of an antigen or an antibody or as quantitative tests to measure the level of antibodies to particulate antigens. Rapid Plate Tests (RPT) or Plate Agglutination Tests (PAT)/Slide Agglutination Tests (SAT) are screening tests used to detect antibodies to microorganisms in the sera. Positive serum samples are subjected to Tube Agglutination Test (TAT) for further confirmation and quantitation of the titer of antibodies. In quantitative test, serial dilutions are made of a serum sample to be tested for antibody and then a fixed amount of particulate antigen is added. The maximum dilution that gives visible agglutination is called the titer. The intensity of the agglutination reaction is a good indicator of the concentration of antibody in the serum. Very low concentration of antibodies may not give visible agglutination. The lack of agglutination at high concentrations of antigen or antibodies is called the Prozone effect. In Prozone very small complexes are formed that do not clump to form visible agglutination. These factors also lead to false negative results.

In many countries, the standard Plate Agglutination Test is the routine test for human Brucellosis. However, it may give false negative results (WHO Report, 1986; Lucero and Bolpe, 1998). Rose Bengal Plate Test (RBPT) is a variant of plate/slide agglutination test where killed *Brucella* organisms stained with Rose Bengal dye are used as antigen for detection of antibodies in the serum. The International Office of Epizootics has recommended the RBPT as one of the tests for the diagnosis of bovine Brucellosis (Corbel and MacMillan, 1995). The RBPT is a quick, cheap and effective test for the diagnosis of Brucellosis. It can be carried out with the minimum of equipment, and the end result is read by the naked eye. However, many factors affect the RBPT reactions and their reading. Some people are able to see the finer agglutination while many others cannot. This causes variation in results. Some authors (Saravi et al., 1990) have reported unacceptable rate of false negatives with the RBPT. The sensitivity of RBPT antigens obtained from different sources may vary considerably when used for testing sera from animals in herds/flocks of low prevalence (Blasco et al., 1994).

The conventional agglutination test is a simple and cheap method for diagnosis of infectious diseases. However, it has lesser sensitivity and hence more chances of false negative results compared to other serological tests like ELISA, Western Blotting etc. Earlier attempts to enhance agglutination have led to the development of Indirect Coombs' Test and Coagglutination Test. The Indirect Coombs' Test using antiglobulin has been applied for cross linking of serum antibodies to make larger clumps of agglutinates for easy detection. However, antiglobulin alone forms spread-out meshwork of antibodies with loose ends of antiglobulin which are difficult to detect with the naked eye. Coagglutination is a sensitive test for screening and rapid diagnosis of infectious diseases. However, it requires Protein A which binds to the immunoglobulins in a non-specific manner and is expensive as well as cumbersome to prepare. Furthermore, false positive results are possible in both, the Coombs' ntiglobulin Test as well as the Coagglutination Test due to the inability to differentiate non-specific aggregates of antigen particles alone from the specific agglutinates formed by antigen and antibody combined.

Limitations of the currently available diagnostic tests include:
a) The available agglutination tests and kits based on them have less sensitivity and more chances of false negative results.
b) Inability to differentiate non-specific aggregates of particulate antigen formed by improper mixing from the specific agglutinates of antigen and antibody may lead to false positive results in conventional agglutination tests.
c) The Indirect Coombs' test using antiglobulin has been applied for cross linking of serum antibodies to make larger clumps of agglutinates for easy detection. However, antiglobulin alone forms widely spread-out meshwork of antigen-antibody clumps with loose ends of antibody bound antiglobulin difficult to detect with the naked eye.
d) Coagglutination Test is dependent on Protein A which is expensive and binds non-specifically to immunoglobulins.
e) False positive results are possible in both, the Coombs' Antiglobulin Test as well as the Coagglutination Test due to the inability to differentiate non-specific aggregates of antigen particles alone from the specific agglutinates formed by antigen and antibody combined.
f) ELISA and Western Blotting require trained technicians and well equipped labs which are few in developing countries. Kits based on these assays are expensive.
g) Molecular diagnostic techniques can be performed only by well trained technicians in well equipped laboratories which are few in developing countries. Commercially available kits based on these assays are expensive.

OBJECTS OF THE INVENTION

An object of this invention is to propose a modified method of agglutination to detect infections caused by various microorganisms.

Another object of this invention is to propose a method for developing an extremely sensitive, specific, cheap and easy to use diagnostic assay and diagnostic kits based on it for infectious diseases.

Still another object of this invention is to propose a method for accurately diagnosing and for rapid screening and monitoring a large number of infectious diseases;

Further, object of this invention is to propose a method to develop a reliable agglutination test to eliminate the possibility of false positive results common with the conventional agglutination tests.

Still further object of this invention is to propose a method to develop a reliable agglutination test to eliminate the possibility of false negative results common with the conventional agglutination tests.

Yet another object of this invention is to propose a diagnostic method and a diagnostic kit based on it which is pen-side and whose result is easily detectable by naked eyes.

BRIEF DESCRIPTION OF THE INVENTION

A modified method of agglutination to detect infections caused by microorganisms comprising:

staining the test serum, plasma or blood or purified antibodies with a protein stain; mixing serum, plasma or blood with stained antibodies with equal quantity of colored which antigen particles on a glass slide;

adding diluted Antiglobulin conjugated with Biotin to the said mixture; subjecting the mixture to the step of mixing; adding diluted Avidin (preferably tagged with a visible indicator) to the mixture and thoroughly mixing all the ingredients.

BRIEF DESCRIPTION OF THE ACCOMPANYING DRAWINGS

FIG. 1. Conventional agglutination with antigen (Ag) and positive serum (Ab).

FIG. 2. Enhanced agglutination with IgG and IgM Antiglobulins (AG).

FIG. 3. Superagglutination with Biotinylated Antiglobulin (bAG) and Avidin (Av).

FIG. 4. Normal Agglutination caused by antigen and positive serum.

FIG. 5. Superagglutination with stained antibody, Biotinylated Antiglobulin and Avidin (gross view).

FIG. 6. Superagglutination (microscopic view).

DETAILED DESCRIPTION OF THE INVENTION

The reaction of a particulate antigen with the antibody leads to the clumping of the antigen which is called Agglutination. The Agglutination test is used in the diagnosis of infections by demonstrating the presence of antibodies in the serum, plasma or blood against antigens of infectious microorganisms. The agglutination test only works with particulate antigens. However, it is possible to coat particles such as latex beads with a soluble antigen (e.g., viral antigen) and use the coated particles in an agglutination test for detecting antibody to the soluble antigen as well. In the Latex Agglutination Test, a suspension of microscopic latex beads coated with the antigen, are mixed with a sample of serum, plasma or whole blood. If antibodies are present in the sample, they will bind to the antigen on the beads causing them to agglutinate or clump. This clumping can be detected visually. Agglutination test is very quick as it can detect antibodies within five minutes compared to several hours it takes to develop results using kits based on other tests.

The agglutination test is a simple and cheap method for the diagnosis of infectious diseases. However, it has lesser sensitivity and hence more chances of false negative results compared to other serological tests like ELISA, Western Blotting etc. Earlier attempts to enhance agglutination have led to the development of Indirect Coombs' test (Coombs' Antiglobulin Test) and Coagglutination test. However, the Coombs' Antiglobulin Test has the limitation of formation of wider meshworks of antigen-antibody clumps due to the loose ends of antiglobulin Fc region. Coagglutination is a sensitive test for screening and rapid diagnosis of infectious diseases. However, it requires Protein A which binds to the immunoglobulins in a non-specific manner and is expensive as well as cumbersome to prepare. Furthermore, false positive results are possible in both, the Coombs' Antiglobulin Test as well as the Coagglutination Test due to the inability to differentiate non-specific aggregates of antigen particles alone from the specific agglutinates formed by antigen and antibody combined. Novel modifications to the conventional agglutination tests (like RBPT, PAT and SAT) presented here can eliminate false positive results by differentiating non-specific aggregates of antigen particles from specific agglutinates of antigen and antibody and can circumvent the problem of false negative results by enhancing their sensitivity multifolds (from two- to ten-folds) without affecting the specificity. In the modified plate/slide agglutination test, 3 µl (or 1 drop) of the particulate antigen (e.g., Rose Bengal stained, killed *Brucella* organisms in case of RBPT) or antigen coated particles (like latex beads) are mixed with 3 µl (or 1 drop) of the test serum, plasma or blood or purified antibodies on a glass plate or a glass slide as in the conventional method. However, in the modified test, the test serum, plasma or purified antibodies are prestained by mixing with 2-3 µl of a protein stain of contrasting color (like Coomassie Blue or Amido Black) to color the antibodies. Then 3 µl (or 1 drop) of appropriately diluted antiglobulin (antibodies to immunoglobulins, specific to the species of origin and isotype of the test antibody) conjugated with Biotin is added to the reaction mixture (i.e., colored antigen and stained antibody) and the three reactants (viz. colored antigen, stained antibody and Biotinylated Antiglobulin) are then mixed by rocking for four minutes or with the help of a clean toothpick or a micropipette tip. Three microliters of appropriately diluted Avidin (or Avidin conjugated with a visible indicator like Ferritin) are then added to the mixture and the four reactants (viz. colored antigen, stained antibody, Biotinylated Antiglobulin and Avidin) are then mixed thoroughly using a clean toothpick or a micropipette tip. Since Avidin has a strong affinity for Biotin, it will cross-link Biotinylated Antiglobulin bound to the antigen-antibody clumps making larger and more compact masses of clumps. The additional steps of staining the test antibody and adding Biotinylated Antiglobulin and Avidin are the three new modifications to the conventional method of agglutination tests.

The result is read out by the unaided eye or with the help of a hand lens or under an ordinary light microscope after putting a coverslip on the slide. If visible clumps are formed, the test sample is positive for the antibody against that antigen. The above concept can be suitably adapted for application in Standard Tube Agglutination Test (STAT) also. In antibody control (i.e., antigen, negative serum and species—specific antiglobulin), there will be o agglutination of antigen particles. In antiglobulin control (i.e., antigen, positive serum and unrelated antiglobulin), there will be normal agglutination but no enhancement of agglutination. The principle is illustrated with diagrams (FIGS. 1, 2 & 3) and with the photographs of actual results of superagglutination for diagnosis of Brucellosis (FIGS. 4 to 6).

These simple and easy modifications very significantly enhance the sensitivity of the agglutination test because of formation of compact and larger clumps due to cross-linking of antigen-bound antibodies by Biotinylated Antiglobulin cross-linked with Avidin, without compromising specificity and hence minimize the chances of false negative results occurring due to low titer of antibody in the serum or because of Prozone due to antigen or antibody excess. The staining of antibody in the serum/plasma eliminates the false positive results arising due to non-specific aggregates of antigen particles caused by improper mixing. The real agglutinates will be of two colors due to the colored antigen and the stained antibody whereas clumps of antigen particles alone will be of one color only.

The new modifications in the agglutination test proposed here do not require any extra equipment and they do not cost much since only a few microliters of the stain, the diluted Biotinylated Antiglobulin and diluted Avidin are required for each test. Polyclonal antiglobulins from serum can also be used instead of expensive commercially available monoclonal antiglobulins. Furthermore, the additional steps of staining the antibody, adding Biotinylated Antiglobulin and Avidin and mixing the reactants do not require more than five minutes. The antiglobulin of IgG isotype, being bivalent, can give about two-fold enhancement in agglutination whereas, the antiglobulin of IgM isotype, due to its ten binding sites, can give up to ten-fold enhancement in agglutination. The binding of Avidin with Biotin on the Biotinylated Antiglobulin makes the clumps larger and more compact and hence easily detectable by naked eyes. The modified agglutination test as proposed above is named as "Superagglutination Test".

The Agglutination Test is useful when a quick screening result is required, and can be used when other types of antibody detection tests cannot be performed because of the lack of refrigeration and sophisticated equipment. It is particularly useful in remote areas of the world that lack the facilities for other advanced tests and may also be very useful as a preliminary screening measure in emergency situations in the developing countries. Agglutination Tests can be used as qualitative tests to assay for the presence of an antigen or antibody or as quantitative tests to measure the level of antibodies to particulate antigens. Rapid Plate Tests (RPT) or Plate Agglutination Tests (PAT)/Slide Agglutination Tests (SAT) are screening tests used to detect antibodies to microorganisms in the sera. Positive serum samples are subjected to the Standard Tube Agglutination Test (STAT) for further confirmation and quantitation of the titer of antibodies. In quantitative test, serial dilutions are made of a serum sample to be tested for antibody and then a fixed amount of particulate antigen is added. The maximum dilution that gives visible agglutination is called the titer. The intensity of the agglutination reaction is a good indicator of the concentration of antibody in the serum. Very low concentration of antibodies may not give visible agglutination. The lack of agglutination at high concentrations of antigen or antibodies is called the Prozone effect. In Prozone, very small complexes are formed that do not clump to form visible agglutination. These factors lead to false negative results.

In many countries, the standard Plate Agglutination Test is the routine test for human Brucellosis. However, it may give false negative results (WHO Report, 1986; Lucero and Bolpe, 1998). Rose Bengal Plate Test (RBPT) is a variant of plate/slide agglutination test where killed *Brucella* organisms stained with Rose Bengal dye are used as antigen for detection of antibodies in the serum. The International Office of Epizootics has recommended the RBPT as one of the tests for the diagnosis of bovine Brucellosis (Corbel and MacMillan, 1995). The RBPT is a quick, cheap and effective test for the diagnosis of Brucellosis. It can be carried out with the minimum of equipment, and the end result is read by the naked eye. However, many factors affect the RBPT reactions and their reading. Some people are able to see the finer agglutination while many others cannot. This causes variation in results. Some authors (Saravi et al., 1990) have reported unacceptable rate of false negatives with the RBPT. The sensitivity of RBPT antigens obtained from different sources may vary considerably when used for testing sera from animals in herds/flocks of low prevalence (Blasco et al., 1994).

The use of Biotin conjugated Antiglobulin reactive to the agglutinating antibody causes cross-linking of the antibodies. This additional linking of antibody clumped to antigen-coated particles (or particulate antigen) by the Biotinylated Antiglobulin results into larger clumps which are further made larger, compact and consolidated by Avidin binding to Biotin and thus easily visible by the unaided eye. The use of prestained antibodies helps in differentiating non-specific clumps of particulate antigen of single color from the specific antigen-antibody agglutinates with two colors. The addition of Biotinylated Antiglobulin and Avidin to enhance the agglutination (clumping of antigen particles with the antibody) and the staining of test antibodies are the novel ideas and the inventive steps to this invention. The Biotinylated Antiglobulin cross-links the antibody molecules which are clumped to the antigen particles and the Avidin further links the Biotinylated Antiglobulin molecules. Hence larger and compact clumps are formed (i.e., superagglutination occurs) which can be easily detected by the unaided eye.

I claim:

1. A method of agglutination to detect infections caused by microorganisms comprising:
    staining a sample comprising antibodies with a protein stain;
    mixing the stained sample comprising stained antibodies with an equal quantity of colored antigen particles on a glass slide or plate to produce a mixture of antibody-antigen complexes;
    adding diluted antiglobulin conjugated with Biotin to the mixture, thereby forming a mixture of antiglobulin-bound complexes;
    subjecting the mixture of antiglobulin-bound complexes to the step of mixing;
    adding diluted Avidin to the mixture to cross-link the antiglobulin-bound complexes and mixing all the ingredients; and
    detecting agglutination in the mixture of antiglobulin-bound complexes and correlating the presence of agglutination with the presence of an infection.

2. The method as claimed in claim 1, wherein the colored antigen particles that are used are selected from the group consisting of Rose Bengal stained, killed *Brucella* organisms and latex beads or microparticles coated with the antigen.

3. The method as claimed in claim 1, wherein the protein stain that is used to stain the antibody is selected from the group consisting of Coomassie Blue and Amido Black.

4. The method as claimed in claim 1, wherein the antiglobulin conjugated with Biotin is selected from the group consisting of IgG and IgM.

5. The method as claimed in claim 4, wherein IgG causes up to a two-fold enhancement in agglutination and wherein IgM causes up to a ten-fold enhancement in agglutination.

6. The method as claimed in claim 1, wherein the diluted Avidin is tagged with a visible indicator.

7. The method as claimed in claim 6, wherein the visible indicator is ferritin.

* * * * *